(12) United States Patent
Tamai et al.

(10) Patent No.: US 9,510,884 B2
(45) Date of Patent: Dec. 6, 2016

(54) BIODEGRADABLE IMPLANT AND FABRICATION METHOD THEREOF

(71) Applicant: OLYMPUS CORPORATION, Tokyo (JP)

(72) Inventors: Masato Tamai, Hachioji (JP); Takamitsu Sakamoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 624 days.

(21) Appl. No.: 13/943,947

(22) Filed: Jul. 17, 2013

(65) Prior Publication Data

US 2013/0304134 A1 Nov. 14, 2013

Related U.S. Application Data

(63) Continuation of application No. PCT/JP2012/051202, filed on Jan. 20, 2012.

(30) Foreign Application Priority Data

Jan. 24, 2011 (JP) .................................. 2011-012359
Jan. 11, 2012 (JP) .................................. 2012-003547

(51) Int. Cl.
*A61L 27/00* (2006.01)
*A61B 17/86* (2006.01)
(Continued)

(52) U.S. Cl.
CPC ............ *A61B 17/866* (2013.01); *A61L 27/047* (2013.01); *A61L 27/306* (2013.01); *A61L 27/58* (2013.01);
(Continued)

(58) Field of Classification Search
CPC ................ A61F 2210/0004; A61F 2210/0009; A61L 27/047
(Continued)

(56) References Cited

U.S. PATENT DOCUMENTS 8,888,841 B2 * 11/2014 Pandelidis ............ A61L 27/047
623/1.15
9,333,099 B2 * 5/2016 Pacetti ...................... A61F 2/82
(Continued)

FOREIGN PATENT DOCUMENTS

CN 101484599 A 7/2009
EP 1 997 522 A1 12/2008
(Continued)

OTHER PUBLICATIONS

Gray-Munro, J.E. et al., "Influence of surface of modification on the in vitro corrosion rate of magnesium alloy AZ31", Journal of Biomedical Materials Research (2009), vol. 91, No. 1, pp. 221-230.
(Continued)

*Primary Examiner* — David Bates
(74) *Attorney, Agent, or Firm* — Scully, Scott, Murphy & Presser, P.C.

(57) ABSTRACT

The present invention can suitably be used even in a site where hydrogen gas is metabolized slowly, such as the osseous tissue. Provided is a biodegradable implant including a biodegradable magnesium member formed of a magnesium alloy and coating layers that coat the biodegradable magnesium member, thereby reducing the degradation rate thereof in a living organism, wherein a depression to be infiltrated by an osteoblast is formed in a surface of the biodegradable magnesium member.

18 Claims, 12 Drawing Sheets

(51) Int. Cl.
*A61L 27/04* (2006.01)
*A61L 27/58* (2006.01)
*A61L 27/30* (2006.01)

(52) U.S. Cl.
CPC .... *A61F 2210/0004* (2013.01); *A61L 2430/02* (2013.01)

(58) Field of Classification Search
USPC .......................................................... 606/70
See application file for complete search history.

(56) References Cited

U.S. PATENT DOCUMENTS

| | | | |
|---|---|---|---|
| 2008/0249638 A1* | 10/2008 | Asgari ..................... | A61F 2/28 623/23.75 |
| 2009/0081313 A1 | 3/2009 | Aghion et al. | |
| 2009/0131540 A1 | 5/2009 | Hiromoto et al. | |
| 2010/0049299 A1 | 2/2010 | Popowski et al. | |
| 2010/0075162 A1* | 3/2010 | Yang .................. | A61F 2/30767 428/457 |
| 2010/0161031 A1 | 6/2010 | Papirov et al. | |
| 2011/0313527 A1* | 12/2011 | Witte ................. | A61B 17/0401 623/11.11 |
| 2016/0060784 A1* | 3/2016 | Taniguchi .............. | A61B 17/68 428/471 |
| 2016/0213501 A1* | 7/2016 | Pacetti ................... | A61F 2/915 |

FOREIGN PATENT DOCUMENTS

| | | |
|---|---|---|
| JP | 2008-125622 A | 6/2008 |
| JP | 2009-530496 A | 8/2009 |
| JP | 2009-535504 A | 10/2009 |
| JP | 2010-528188 A | 8/2010 |
| WO | WO 2007/108450 A1 | 9/2007 |

OTHER PUBLICATIONS

Supplit, R. et al., "Evaluation of the anti-corrosive effect of acid pickling and sol-gel coating on magnesium AZ31 alloy", Corrosion Science (2007), vol. 49, No. 7, pp. 3015-3023.
Hanzi, A.C. et al., "On the biodegradation performance of an Mg—Y—RE alloy with various surface conditions in simulated body fluid", Acta Biomaterialia (2009), vol. 5, No. 1, pp. 162-171.
Murkami, Koji et al., "Mechanism of Corrosion Protection of Magnesium Alloys Anodized by Phosphate Electrolyte", Journal of the Japan Institute of Metals (2009), vol. 73, No. 5, pp. 354-361.
Murakami, Koji et al., "Mechanism of Corrosion Protection of Anodized Magnesium Alloys", Materials Transactions (2008), vol. 49, No. 5, pp. 1057-1064.
Murakami, Koji et al., "Corrosion protection of AZ91D magnesium alloy by anodization using phosphate electrolyte", Journal of Japan Institute of Light Metals (2008), vol. 58, No. 8, pp. 381-387.
Murakami, Koji et al., "Corrosion Protection of AZ91D Magnesium Alloy of Anodization Using Phosphate Electrolyte", Materials Transactions (2007), vol. 48, No. 12, pp. 3101-3108.
Sakai, Koji et al., "Magnesium Seihin no Kankyo Chowa-gata Yokyoku Sanka Shori no Kaihatsu", Materia Japan (2004), vol. 43, No. 1, pp. 52-54.
International Search Report dated Feb. 28, 2012 issued in PCT/JP2012/051202.
Liu, M., et al., "The influence of yttrium (Y) on the corrosion of Mg—Y binary alloys", 2010, Corrosion Science 52, pp. 3687-3701.
Extended Supplementary European Search Report dated Mar. 2, 2015 from related European Application No. 12 73 9295.9.

* cited by examiner

BIODEGRADABLE IMPLANT AND FABRICATION METHOD THEREOF

CROSS-REFERENCE TO RELATED APPLICATIONS

This is a continuation of International Application PCT/JP2012/051202, with an international filing date of Jan. 20, 2012, which is hereby incorporated by reference herein in its entirety. This application claims the benefit of Japanese Patent Application No. 2011-012359 and Japanese Patent Application No. 2012-003547, the contents of which are incorporated herein by reference.

TECHNICAL FIELD

The present invention relates to a biodegradable implant that is employed in, for example, the medical field and that is embedded in a living organism, as well as to a fabrication method thereof.

BACKGROUND ART

With the practice in the orthopedic field, metal devices of titanium, stainless steel, and so forth are generally used as high-strength device for securing an injury (plates, screws, pins, etc.). Because these high-strength materials do not degrade in a living organism and remain in the living organism after fracture treatment, a second surgery is required to remove them. Thus, in order to eliminate the need for the second surgery, amorphous or semicrystalline bioabsorbent polymers, such as, for example, polyglycolic acid (PGA), polylactic acid (PLA), or the like, are used.

The ideal property of a biodegradable implant used in fracture treatment is that it should degrade and be replaced by bones within an appropriate amount of time. However, these materials do not have sufficient strength for use under high-load conditions, and there is a problem in that they cannot be used in applications in which high load is exerted thereon.

In response to the above-described problem, there have been known attempts to employ magnesium alloys as biodegradable implants (for example, see Patent Literature 1). Medical use of magnesium alloys has been considered because they have higher strength and are more biodegradable than PLA.

By undergoing chemical reactions with ions in water or body fluid in a living organism, magnesium alloys form calcium phosphate, which is a corrosion product, at the surface thereof, and also generate hydrogen gas. Once the surface of an implant is covered with the corrosion product, the rate of the above-described corrosion reaction drops, and the corrosion product, on the other hand, is phagocytosed by macrophages in the living organism. Due to this reaction in the living organism, the metal surface of the implant becomes exposed, and the biodegradation reaction on the implant is thought to advance due to the above-described corrosion reaction that advances over time.

Once the corrosion product is formed in a living organism, an implant made of a magnesium alloy takes a form whose influence on biological tissue is sufficiently low due to the suppressed generation of hydrogen gas; however, during an early stage in use of the implant before the corrosion product is sufficiently formed, a large amount of hydrogen gas is generated. In order to apply a magnesium alloy to an implant, this generation of hydrogen gas during the early stage in use of the implant should be suppressed, and as a means of achieving this, an anodic oxide layer is formed on the surface of a biodegradable implant to achieve passivation thereof (for example, see Patent Literature 2).

CITATION LIST

Patent Literature

{Patent Literature 1} Japanese Unexamined Patent Application, Publication No. 2008-125622
{Patent Literature 2} Japanese Translation of PCT International Application, Publication No. 2009-535504

SUMMARY OF INVENTION

A first aspect of the present invention is a biodegradable implant including a biodegradable magnesium member formed of a magnesium alloy; and a coating layer that coats the biodegradable magnesium member, thereby reducing a degradation rate thereof in a living organism, wherein a depression to be infiltrated by an osteoblast is formed in a surface of the biodegradable magnesium member.

A second aspect of the present invention is a biodegradable implant fabrication method including a coating step of coating a surface of a biodegradable magnesium member formed of a magnesium alloy with a coating layer that reduces a degradation rate in a living organism, and a depression forming step of forming a depression to be infiltrated by an osteoblast in a surface of the biodegradable magnesium member before the coating step.

DESCRIPTION OF EMBODIMENTS

First Embodiment

A biodegradable implant and a fabrication method thereof according to a first embodiment of the present invention will be described below with reference to the drawings.

Figure 1:
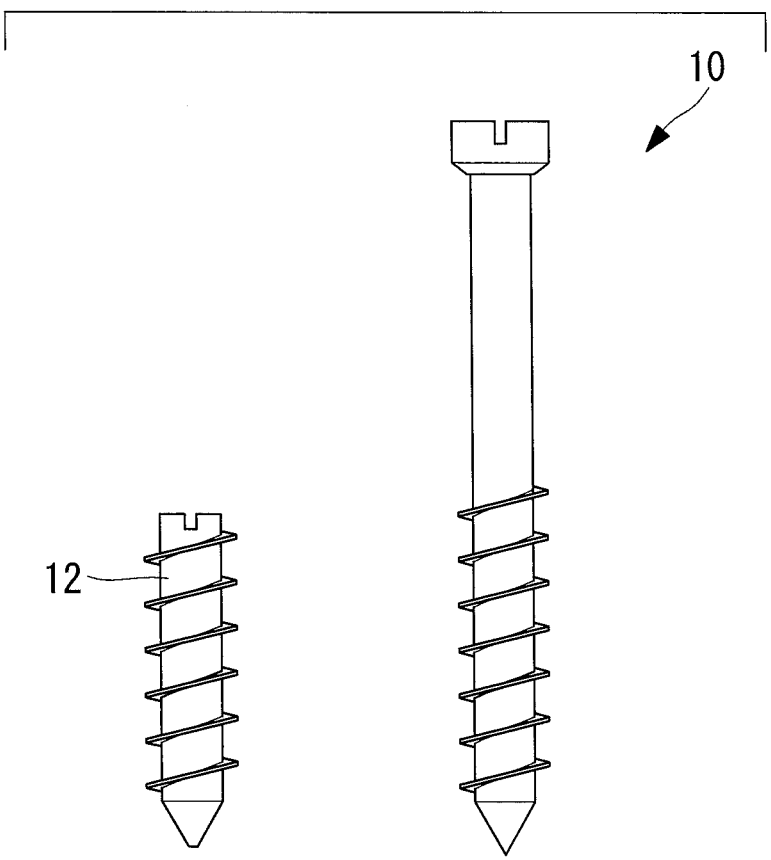
FIG. 1 is a front view of an implant substrate (for embedding usage) according to a first embodiment of the present invention.
Figure 2:
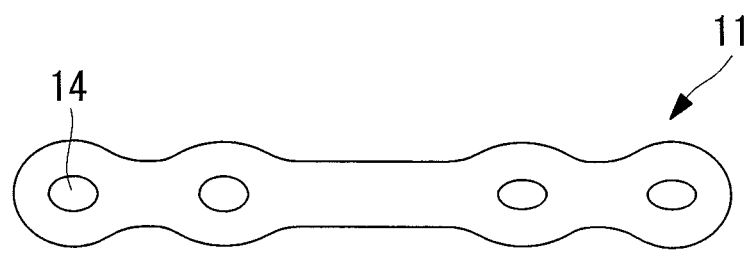
FIG. 2 is a front view of an implant substrate (for securing usage) according to the first embodiment of the present invention.

The biodegradable implant according to this embodiment is provided with implant substrates (biodegradable magnesium members) 10 and 11, shown in FIGS. 1 and 2, and anodic oxide layers (see FIG. 6) formed so as to coat surfaces of the implant substrates 10 and 11.

The implant substrates 10 and 11 are formed of a magnesium alloy, which degrades in a living organism, and, for example, a WE43 alloy that contains rare earth elements, such as, for example, neodymium, zirconium, and so forth, is employed. By employing such a magnesium alloy containing rare earth elements, it is possible to enhance the strength of the implant substrates 10 and 11.

The shapes of the implant substrates 10 and 11 take a shape in accordance with the usage thereof, for example, a screw shape or a plate shape. The implant substrates 10 and 11 are corroded and lost in a living organism with the passage of time. This is because magnesium, which is the main component, reacts with water to generate magnesium hydroxide and hydrogen, and the generated magnesium hydroxide is absorbed into the living organism.

The implant substrate 10 shown in FIG. 1 is an implant substrate to be embedded into a bone, and screw-thread-like protrusions 12 are formed at the surface of the implant substrate 10. These protrusions 12 are formed in the axial direction of the implant substrate 10 at a pitch of 1 mm or less. By inserting the implant substrate 10 having such a configuration into a bone, the protrusions 12 engage with the bone, making it possible to secure the implant substrate 10 to the bone. In this case, by forming the protrusions 12 at a pitch of 1 mm or less, it is possible to ensure a desired securing force when the biodegradable implant is secured to the bone.

The implant substrate 11 shown in FIG. 2 is an implant substrate for achieving bone-to-bone connection. Specifically, two bones can be connected by placing the implant substrate 11 at surfaces of the two bones to be connected and by securing the implant substrates 10 to the bones by passing them through holes 14 formed in the implant substrate 11.

Figure 10A:
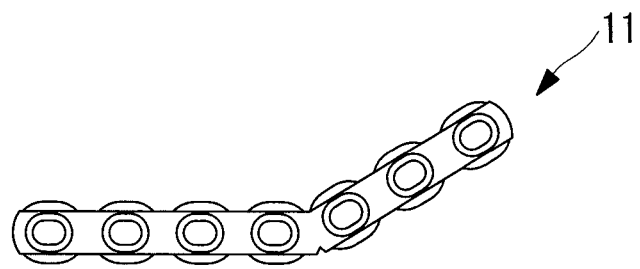
FIG. 10A is a front view of an implant substrate (for securing usage) according to a modification of that in FIG. 2.
Figure 10B:
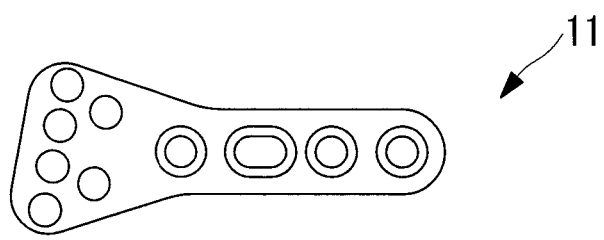
FIG. 10B is a front view of an implant substrate (for securing usage) according to a modification of that in FIG. 2.
Figure 10C:
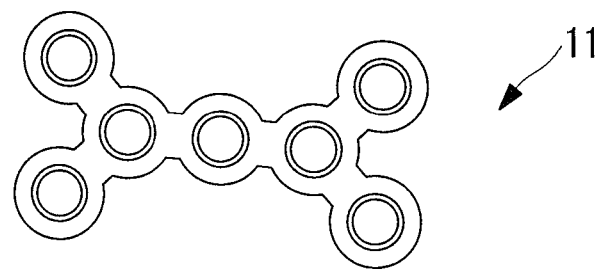
FIG. 10C is a front view of an implant substrate (for securing usage) according to a modification of that in FIG. 2.

Note that the shapes of the implant substrates 10 and 11 are not limited to the above-described shapes, and they may be molded into shapes suitable for the shape of an affected area (bone). For example, the implant substrates 10 and 11 may take a plate shape or a rod shape, as shown in FIGS. 10A to 10C. In the case of a plate, it is desirable that the thickness thereof be 0.5 mm or greater and 5 mm or less, and it is desirable that one or more holes for securing a screw be formed therein (see FIGS. 10A to 10C). In addition, in the case of a rod, it is desirable that the structure thereof be columnar (not shown) to be inserted into the medullary cavity of a bone.

Figure 3:
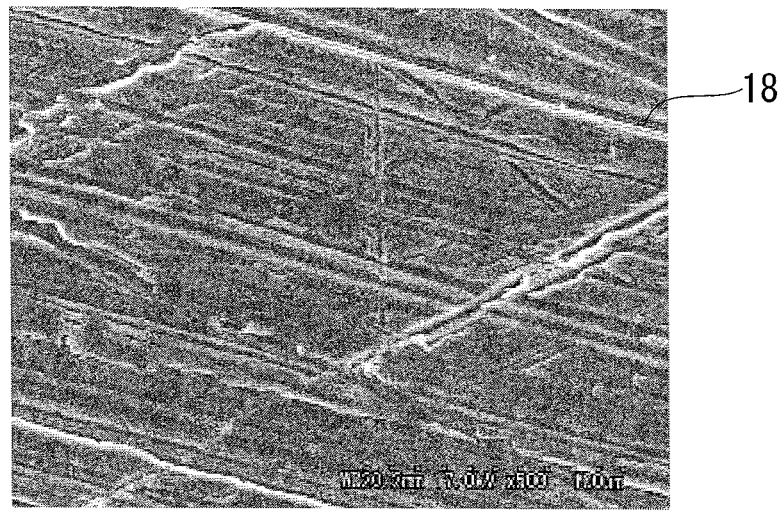
FIG. 3 is magnified views of surfaces of the implant substrates in FIG. 1 and FIG. 2.
Figure 4:
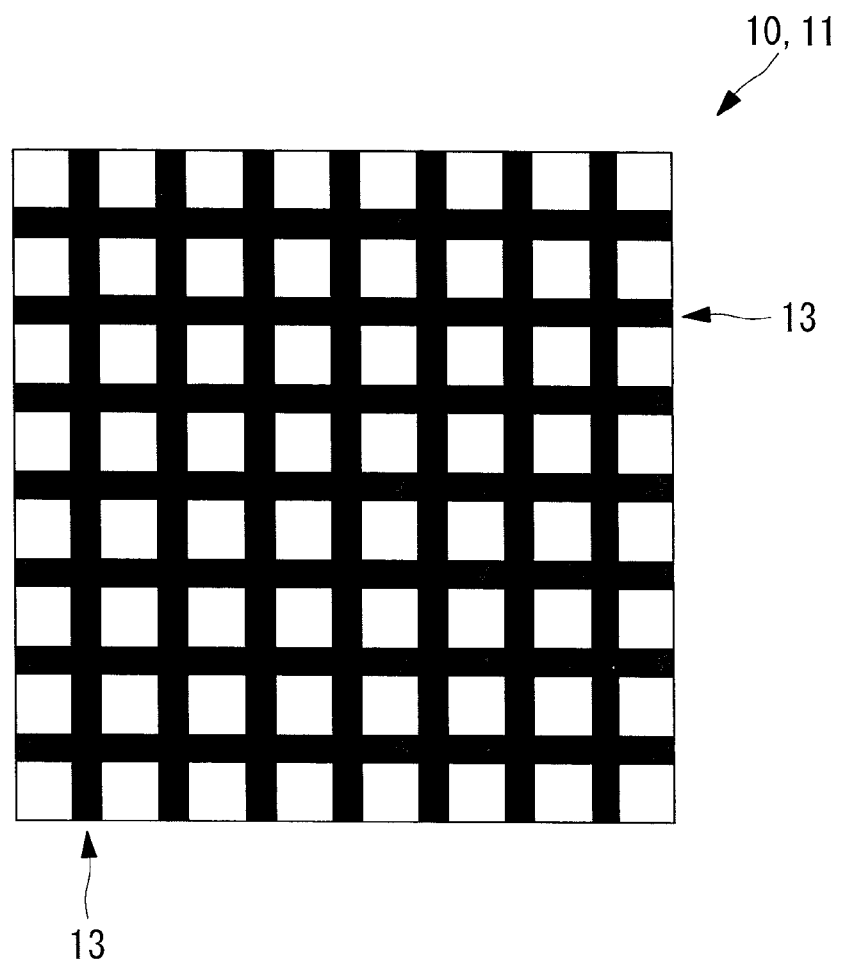
FIG. 4 is a plan view schematically showing depressions in FIG. 3.
Figure 5:
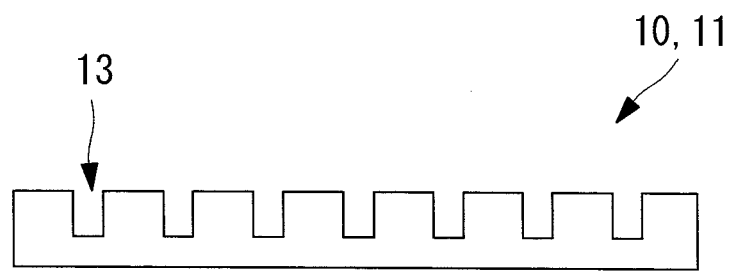
FIG. 5 is a cross-sectional view schematically showing the depressions in FIG. 3.

Depressions 13 like those shown in FIG. 3 are formed in the surfaces of the implant substrates 10 and 11. FIG. 4 and FIG. 5 respectively show a plan view and a cross-sectional view, schematically showing these depressions 13.

As shown in FIGS. 4 and 5, the depressions 13 are grooves formed in the surface of the implant substrate 10 by means of machining or the like, and a plurality of depressions 13 are formed in the surface of the implant substrate 10 in a lattice-like manner.

The depressions 13 are formed so as to have widths of 30 µm or greater and 300 µm or less, and they are formed so as to have depths of 30 µm or greater and 300 µm or less. In addition, the depressions 13 are formed in the surface of the implant substrate 10 so as to be, for example, 100 µm apart.

Figure 6:
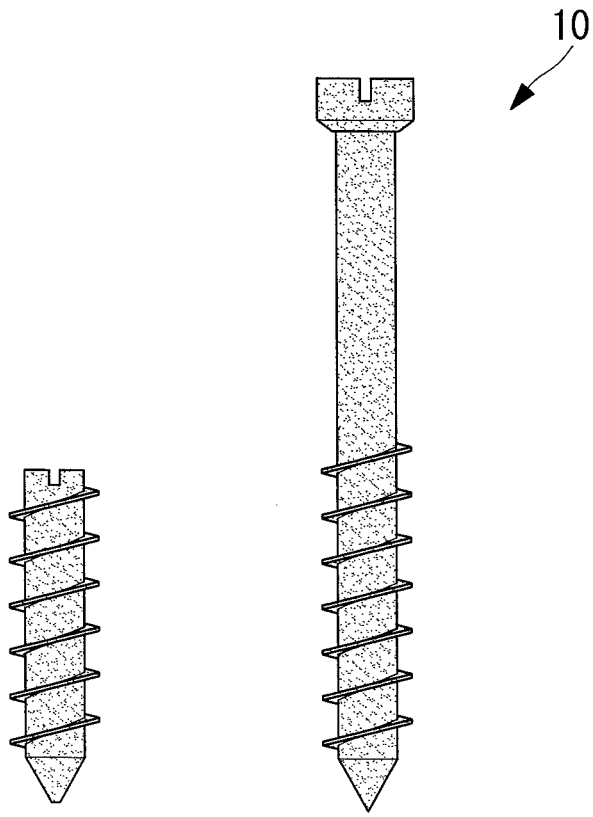
FIG. 6 is a front view showing a state in which anodic oxidation treatment is applied to the implant substrate in FIG. 1.

As shown in FIG. 6, anodic oxide layers (oxide layers or coating layers) are formed on the surfaces of the implant substrates 10 and 11 by means of the anodic oxidation treatment. The anodic oxide layers are constituted mainly of magnesium, oxygen, and phosphorus, and the layer thickness thereof is 0.1 µm or greater and 20 µm or less.

Here, a method is used for the anodic oxidation treatment below. Specifically, the oxide layer is formed by electrochemically oxidizing the target object surfaces of anodes by using the coating target objects (implant substrates 10 and 11) as the anodes in the electrolyte solution and by performing electrolysis by applying a voltage between the anodes and a cathode such as stainless steel or the like. It is preferable that the electrolyte solution contain phosphate ions when performing the anodic oxidation treatment.

The advantageous effects of the biodegradable implant according to this embodiment, having the above-described configuration, will be described below.

Figure 7:
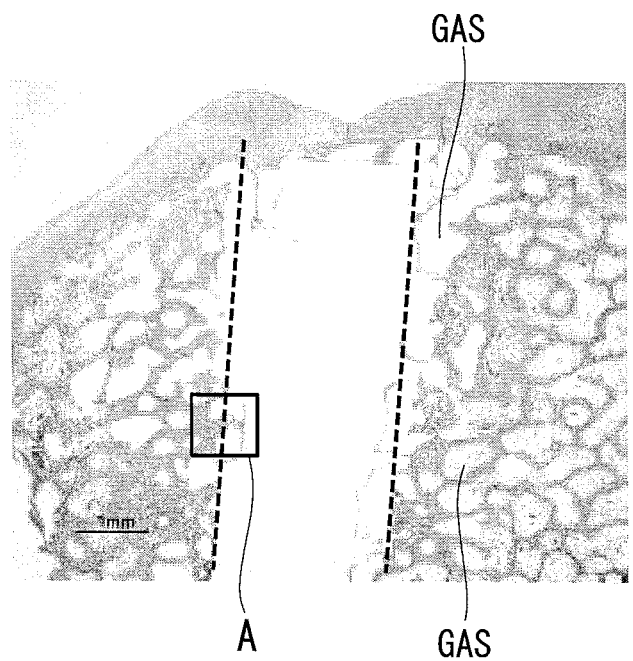
FIG. 7 is a microscope image showing a case in which the biodegradable implant according to the first embodiment of the present invention is embedded in a bone.
Figure 8:
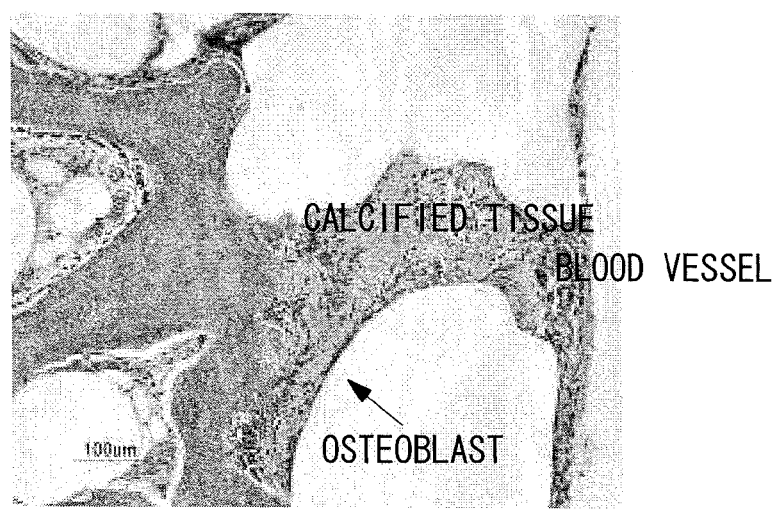
FIG. 8 is a magnified image of a portion A in FIG. 7.
Figure 19:
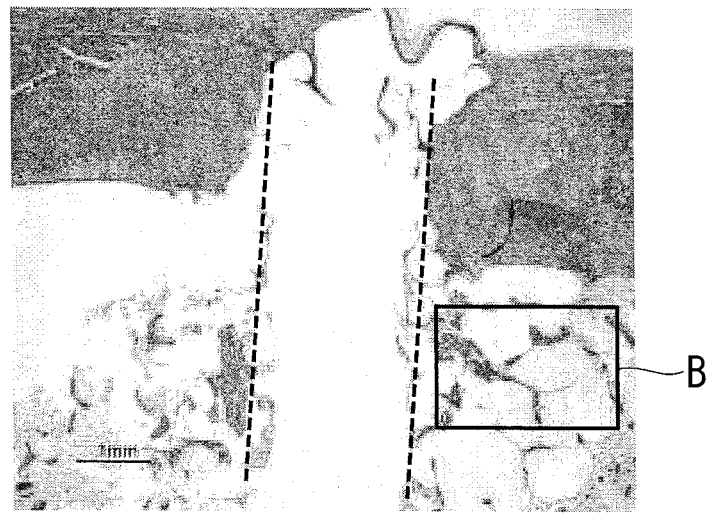
FIG. 19 is a microscope image showing a case in which a conventional biodegradable implant is embedded in a bone.

FIG. 7 shows a microscope image for the case in which the biodegradable implant according to this embodiment is embedded in a bone, and FIG. 8 shows a magnified image of a portion A in FIG. 7. FIG. 19 shows, as a Comparative Example, a microscope image for the case in which a conventional biodegradable implant in which the depressions are not formed is embedded in a bone, and FIG. 20 shows a magnified image of a portion B in FIG. 19.

Figure 20:
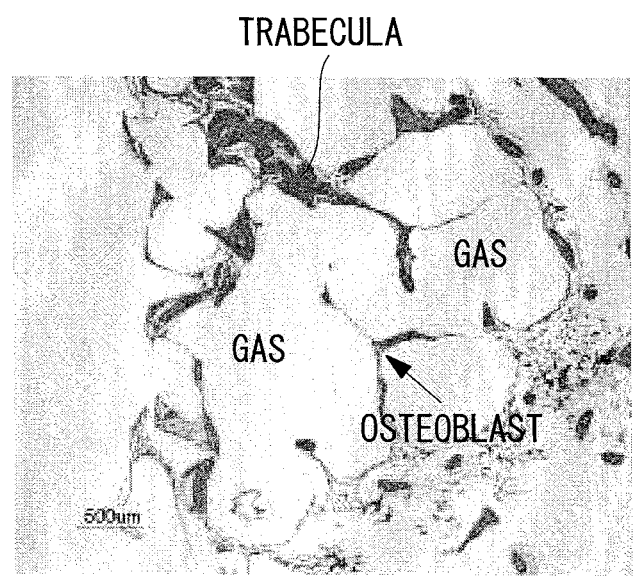
FIG. 20 is a magnified image of a portion B in FIG. 19.

As shown in FIGS. 19 and 20, with the conventional biodegradable implant, the destruction or reduction of trabeculae can be seen in a cancellous bone around portions where the biodegradable implant is embedded (portions indicated by dotted lines in FIG. 19). In addition, a fibrous film can be seen in the surroundings of hydrogen gas generated from the implant substrate. Furthermore, osteocytes and osteoblasts do not exist in the destroyed trabeculae. Additionally, although immunologically inactive, tissue injury due to hydrogen gas or the implant substrate can be seen.

In contrast, as shown in FIGS. 7 and 8, with the biodegradable implant according to this embodiment, although the generation of hydrogen gas can be seen, as with the conventional biodegradable implant, the generation rate of hydrogen gas is suppressed by applying the anodic oxidation treatment. In addition, the destruction or reduction of trabeculae that occurred in the case of the conventional biodegradable implant is not seen. Furthermore, it is found that an osteoid (an immature bone before developing into osseous tissue) is formed so as to infiltrate the biodegradable implant.

As has been described above, with the biodegradable implant according to this embodiment, in a biological subject, the degradation rates of the implant substrates 10 and 11 are kept low by means of the anodic oxide layers that coat the surfaces of the implant substrates 10 and 11. Because of this, the concentration of hydrogen gas generated when the implant substrates 10 and 11 degrade in a living organism can be kept low, and damage to cells due to hydrogen gas can be suppressed. Furthermore, because the depressions 13 are formed in the surfaces of the implant substrates 10 and 11, cells such as osteoblasts or the like can infiltrate the depressions 13, and thus, bone formation can be promoted.

In this case, by forming the depressions 13 so that the widths thereof are 30 μm or greater and 300 μm or less, osteocytes can effectively made to proliferate by facilitating the infiltration by osteoblasts whose sizes are about 100 μm.

In addition, by forming the depressions 13 so that the depths thereof are 30 μm or greater, it is possible to make osteoblasts, whose sizes are about 100 μm, infiltrate effectively. In addition, by forming the depressions 13 so that the depths thereof are 300 μm or less, it is possible to ensure sufficient strength of the biodegradable implants (implant substrates 10 and 11).

Note that, in the biodegradable implant according to this embodiment, the depressions 13 may be holes formed in the surfaces of the implant substrates 10 and 11. In this case, by forming the holes so that the diameters and depths thereof are 30 μm or greater and 300 μm or less, osteocytes can effectively made to proliferate by facilitating the infiltration by osteoblasts.

In addition, in this case, communicating holes that join a plurality of holes may be provided.

By providing such communicating holes, bone formation can be promoted by making osteoblasts effectively infiltrate the depressions 13.

Next, a fabrication method of the biodegradable implant according to this embodiment will be described.

Figure 9:
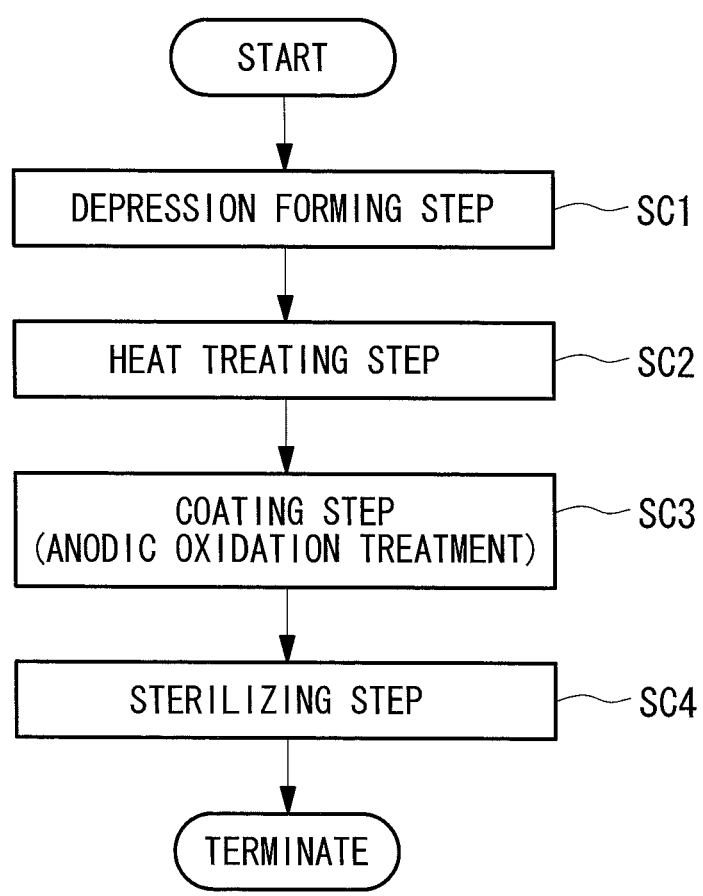
FIG. 9 is a flow chart showing a fabrication method of the biodegradable implant according to the first embodiment of the present invention.

As shown in FIG. 9, a fabrication method of the biodegradable implant according to this embodiment includes a depression forming step SC1 of forming the depressions 13 in the surfaces of the implant substrates 10 and 11, a heat treating step SC2 of subjecting the implant substrates 10 and 11 in which the depressions 13 have been formed to heat treatment, an oxide-layer forming step (coating step or anodic oxidation treatment) SC3 of coating the surfaces of the implant substrates 10 and 11 with the anodic oxide layers, and a sterilizing step SC4 of subjecting the implant substrates 10 and 11 to sterilization treatment.

In the depression forming step SC1, the depressions 13 to be infiltrated by osteoblasts are formed in the surfaces of the implant substrates 10 and 11 constituted of a biodegradable material, by means of, for example, machining such as cutting or the like or hot working.

Next, in the heat treating step SC2, the heat treatment of the implant substrates 10 and 11 is performed under conditions of, for example, a temperature of 525° C. and s heat treatment time of 8 hours. By performing such heat treatment, the constitution of the implant substrates 10 and 11 is made uniform, and thus, the variability of the degradation rates of the implant substrates 10 and 11 in a living organism can be reduced. In addition, the strength of the implant substrates 10 and 11 can be enhanced.

Next, in the oxide-layer forming step SC3, the anodic oxidation treatment is applied by using the implant substrates 10 and 11 as anodes and the stainless steel as a cathode and by immersing these anodes and cathode in the electrolyte solution containing phosphate ions. By doing so, the anodic oxide layers that reduce degradation rates in a living organism are formed on the surfaces of the implant substrates 10 and 11.

In this case, the electrolyte solution is an aqueous alkaline solution containing phosphate ions. More specifically, the electrolyte solution is an aqueous solution that contains 0.1 mol/L or greater and 1 mol/L or less phosphate ions and whose pH is 11 or greater and 13 or less.

Phosphate ions are contained in the electrolyte solution in the form of, for example, phosphate, hydrogen phosphate, dihydrogen phosphate, and so forth.

The pH of the electrolyte solution is adjusted by using an alkaline solution such as, for example, sodium hydroxide, potassium hydroxide, ammonia, and so forth.

As the cathode, for example, stainless steel is employed; however, it is not particularly limited thereto.

The power source for the anodic oxidation treatment is not particularly limited, and it may be a DC power source or an AC power source.

More specifically, the anodic oxidation treatment is performed, for example, under the following conditions.

As the electrolyte solution, an aqueous solution containing, for example, 0.25 mol/L phosphoric acid, 1 mol/L ammonia, and 10 g of sodium hydroxide, is employed.

When the anodic oxidation treatment is performed at a constant current, for example, the current is set to be 0.1 mA, the voltage is assumed to be 200 V or less, and the power-on duration is assumed to be two minutes or less. When the anodic oxidation treatment is performed at a constant voltage, for example, the voltage is set to be 200 V, the current is assumed to be 0 mA or less, and the power-on duration is assumed to be six minutes or less. By doing so, anodic oxide layers whose layer thicknesses are 0.1 μm or greater and 20 μm or less can be formed on the surfaces of the implant substrates 10 and 11.

In the sterilizing step SC4, the biodegradable implant is sterilized by using, for example, ethylene oxide gas (ethylene oxide gas). Note that the sterilization method of the biodegradable implant is not limited to the method described above, and, for example, a sterilization method by using radiation or a sterilization method by using low-temperature hydrogen-peroxide plasma may be employed.

With the biodegradable implant fabricated in this way, the degradation rates of the implant substrates 10 and 11 in a living organism are kept low by means of the anodic oxide layers formed on the surfaces of the implant substrates 10 and 11. Accordingly, the concentration of hydrogen gas generated when the implant substrates 10 and 11 degrade in a living organism can be kept low, and thus, damage to cells due to the hydrogen gas can be suppressed. Furthermore, because the depressions 13 are formed in the surfaces of the implant substrates 10 and 11, cells such as osteoblasts or the like can infiltrate the depressions 13, and thus, bone formation can be promoted.

Second Embodiment

A biodegradable implant 1 and a fabrication method thereof according to a second embodiment of the present invention will be described below with reference to FIGS. 11 and 12.

In the first embodiment, the biodegradable implant is provided with the anodic oxide layer as a coating layer; alternatively, the biodegradable implant according to this embodiment is provide with an intermediate layer formed of high-purity magnesium between the implant substrate and the anodic oxide layers.

Figure 11:
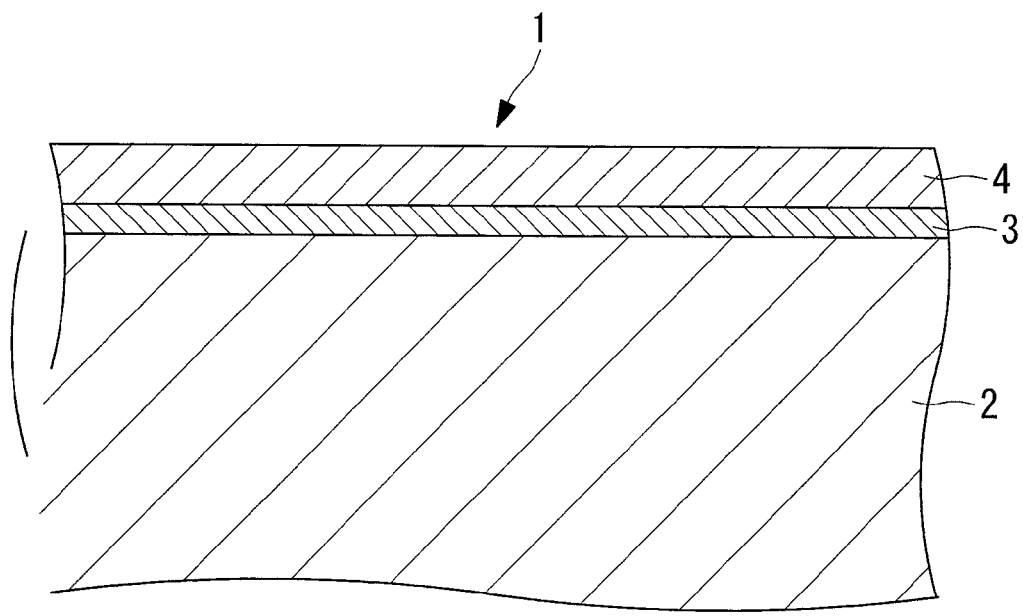
FIG. 11 is a partial cross-sectional view showing the configuration of a biodegradable implant according to a second embodiment of the present invention.

Specifically, as shown in FIG. 11, the biodegradable implant 1 according to this embodiment is provided with an implant substrate (biodegradable magnesium member) 2 that serves as a base material, an intermediate layer (high-purity magnesium layer or coating layer) 3 that coats the surface of the implant substrate 2, and an oxide layer (coating layer) 4 that coats the outer side of the intermediate layer 3.

The implant substrate 2 is formed of a magnesium alloy in which other elements are added to magnesium which is the main component thereof. It is preferable that the magnesium alloy be based on high-strength WE to which elemental yttrium and rare earth elements are added; however, a magnesium alloy that contains other metal elements as additives may be employed. Examples of the other metal elements include electrically more noble metal elements than magnesium or/and rare earth elements. These elements dissolve in an acidic solution when a surface of the implant substrate 2 is exposed to the acidic solution in an acid treating step SA1 described later.

The shape of the implant substrate 2 takes the same shape as the implant substrates 10 and 11 of the first embodiment, for example, the screw shape or the plate shape shown in FIG. 1, 2 or 10. In addition, the depressions 13 shown in FIG. 5 are formed in the surfaces of the implant substrate 2.

The intermediate layer 3 includes magnesium as the main component, and the content rate of metal elements other than magnesium (non-magnesium metals) is lower as compared with that in the implant substrate 2. It is preferable that the content rate of the non-magnesium metals in the intermediate layer 3 be equal to or less than 1/10 of that in the implant substrate 2. When the content rate of the non-magnesium metals in the intermediate layer 3 is greater than 1/10 of that in the implant substrate 2, it is difficult to sufficiently retard the corrosion rate of the intermediate layer 3. It is preferable that the layer thickness of such an intermediate layer 3 be 0.1 μm or greater and 300 μm or less.

The oxide layer 4 is formed of an oxide, and it is preferable that the layer thickness thereof be 0.1 μm or greater and 20 μm or less. The oxide layer 4 formed of a highly corrosion resistant oxide exhibits a sufficiently slower corrosion rate in a living organism than that of the magnesium alloy constituting the implant substrate 2. Therefore, by providing the oxide layer 4 at the outermost side, it is possible to more effectively protect the implant substrate 2 from rapid corrosion.

It is preferable that such an oxide layer 4 be an anodic oxide layer that is constituted mainly of magnesium oxide and that is formed by subjecting the implant substrate 2 coated with the intermediate layer 3 to anodic oxidation treatment. The anodic oxidation treatment is a method of forming an oxide layer by electrochemically oxidizing a target object surface at an anode by using a coating target object (implant substrate 2) as the anode in an electrolyte solution and by performing electrolysis by applying a voltage between the anode and a cathode such as stainless steel or the like. With this method, the anodic oxide layer and the intermediate layer 3 are firmly attached to each other. In addition, there is an advantage in that no special device is required, and the treatment can be completed in a short period of time.

It is more preferable that the anodic oxide layer contain phosphorus, and it is even more preferable that it contains 35 wt % or greater and 65 wt % or less elemental magnesium, 25 wt % or greater and 45 wt % or less elemental oxygen, and 4 wt % or greater and 15 wt % or less elemental phosphorus. By using such a composition, it is possible to enhance the corrosion resistance of the anodic oxide layer. By using an electrolyte solution that contains phosphate ions when performing the anodic oxidation treatment, phosphorus can be added to the anodic oxide layer. The anodic oxide layer containing phosphorus has a sacrificial corrosion protective effect, and thus, it is possible to achieve a high corrosion resistant effect. Furthermore, the presence of phosphorus on the surface of the biodegradable implant 1 makes it possible to increase the biocompatibility of the biodegradable implant 1. It is preferable that the anodic oxide layer additionally contain 5% or greater and 20% or less elemental yttrium.

The effects of the biodegradable implant 1 according to this embodiment, having the above-described configuration, will be described below.

The biodegradable implant 1 according to this embodiment is, for example, a screw for achieving bone-to-bone connection, and is secured to the bones by being inserted into holes formed in the bones.

With the biodegradable implant 1 held at the bones, corrosion of the oxide layer 4 that coats the outermost side of the biodegradable implant 1 is prevented, and thus, the loss of the implant from the implanted site takes a sufficiently long period of time.

In this case, when there is a site from which the oxide layer 4 has been lost because the oxide layer 4 has been sufficiently corroded or partially come off, the intermediate layer 3 becomes exposed. The intermediate layer 3 whose content rate of the non-magnesium metals is relatively low exhibits a slower corrosion rate in a living organism as compared with the magnesium alloy constituting the implant substrate 2. Therefore, there is an advantage in that it is possible to suppress the rapid generation of hydrogen by continuing to prevent the corrosion of the implant substrate 2 by means of the intermediate layer 3 even after the oxide layer 4 is no longer present.

Here, the corrosion of the implant substrate 2 and the intermediate layer 3, whose main components are magnesium, is due to a reaction of magnesium, as described above. This corrosion reaction is promoted by the occurrence of galvanic corrosion at a contact surface between magnesium and the non-magnesium metals. In other words, it is likely that, with the intermediate layer 3 having a relatively low content rate of the non-magnesium metals, the corrosion rate thereof in a living organism will be retarded due to the suppression of galvanic corrosion, as compared with the implant substrate 2.

Next, a method of fabricating the above-described biodegradable implant 1 will be described.

Figure 12:
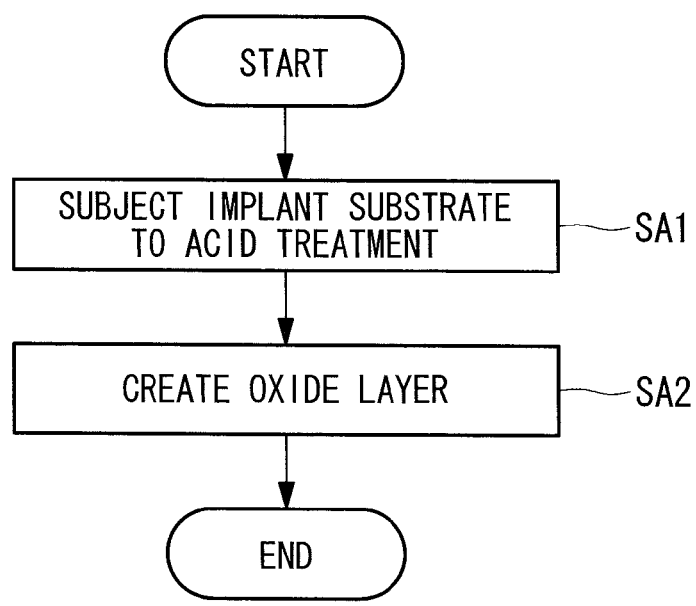
FIG. 12 is a flow chart showing a fabrication method of the biodegradable implant according to the second embodiment of the present invention.
Figure 13:
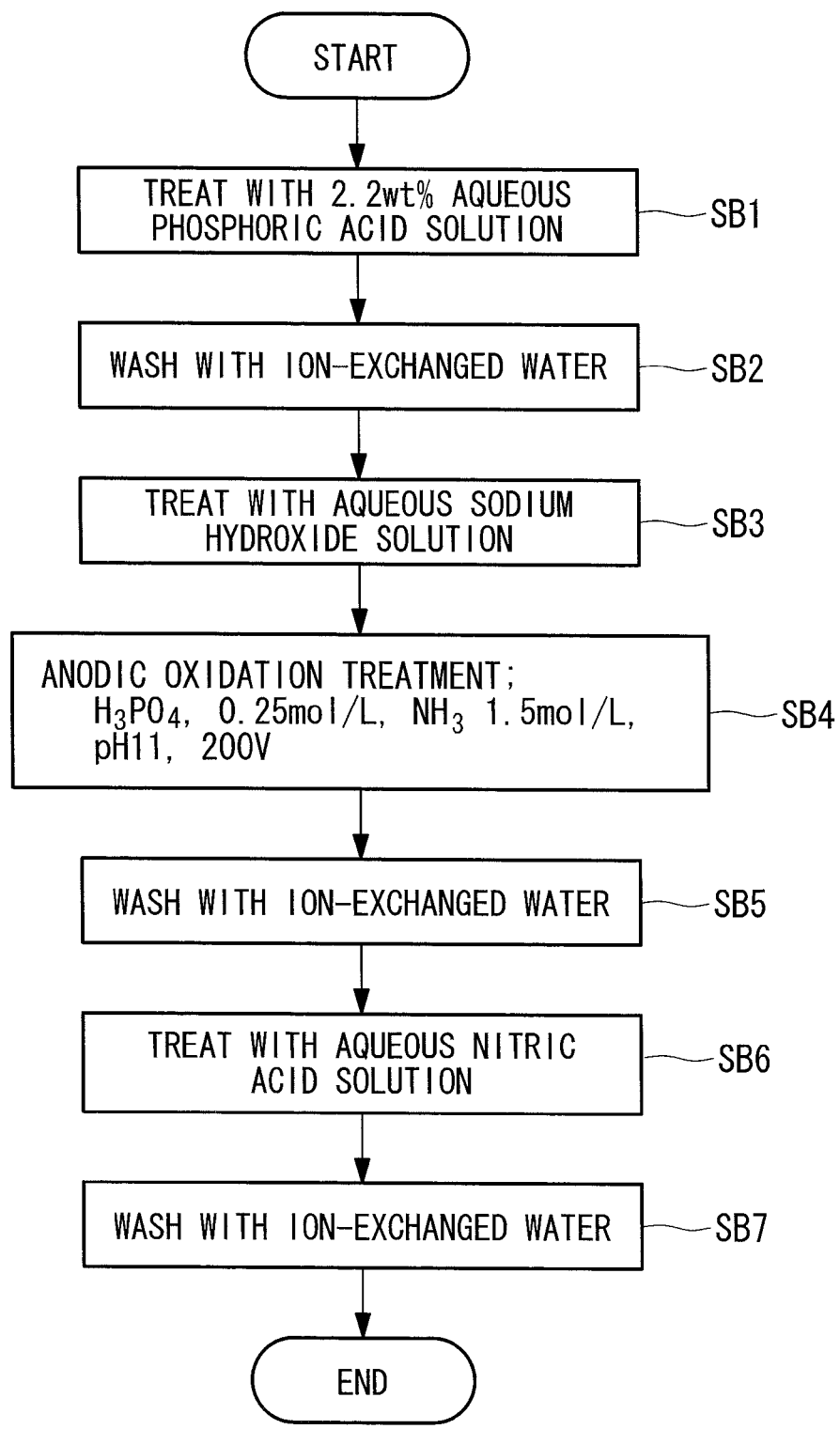
FIG. 13 is a flow chart showing a fabrication method of a biodegradable implant according to an Example of the second embodiment of the present invention.

As shown in FIG. 12, a fabrication method of a biodegradable implant according to this embodiment includes an acid treating step (coating step or high-purity magnesium layer forming step) SA1 of subjecting an implant substrate 2 to acid treatment and an oxide-layer forming step (coating step) SA2 of coating a surface of the acid-treated implant substrate 2 with the oxide layer 4. These steps SA1 and SA2 are performed after the depression forming step SC1 and the heat treating step SC2 described above.

In the acid treating step SA1, the implant substrate 2 is immersed in an acidic solution, subjecting the surface of the implant substrate 2 to the acid treatment. It is preferable that the acidic solution be aqueous phosphoric acid solution, which has high biocompatibility, and 0.5 wt % or greater and 10 wt % or less aqueous phosphoric acid solution is more preferable. The acidic solution degreases the surface of the implant substrate 2. Simultaneously, at a surface layer of the implant substrate 2 immersed in the acidic solution, the non-magnesium metals are removed by reacting with the acidic solution. By doing so, a layer that serves as the intermediate layer 3, whose content rate of the non-magnesium metals is lower than other portions, is formed at the surface layer of the implant substrate 2. Following the acid treatment, by washing the implant substrate 2 with ion-exchanged water or the like, the acidic solution deposited on the surface of the implant substrate 2 is satisfactorily removed.

Next, in the oxide-layer forming step SA2, the implant substrate 2 serving as an anode and stainless steel serving as a cathode are immersed in an electrolyte solution, and anodic oxidation treatment is performed by applying a voltage between these electrodes. By doing so, an anodic oxide layer, whose main component is magnesium oxide (oxide), is formed outside the intermediate layer 3 formed at the surface layer of the implant substrate 2. Note that the cathode is not limited to the stainless steel, and any other material is permissible so long as it is formed of a material that acts as a cathode for the implant substrate 2. In addition, the voltage applied between the positive terminal and the cathode may be a DC voltage or an AC voltage.

In this case, it is preferable that the electrolyte solution be an alkaline aqueous solution containing phosphate ions. More specifically, it is preferable that the electrolyte solution be an aqueous solution that contains 0.2 mol/L or greater and 1 mol/L or less phosphate ions and 0.2 mol/L or greater and 5 mol/L or less ammonia or ammonium ions, whose pH is 11 or greater and 13 or less. The phosphate ions are contained in the electrolyte solution in the form of, for example, phosphate, hydrogenphosphate, dihydrogenphosphate, and so forth. The pH of the electrolyte solution is adjusted by using an alkaline solution such as, for example, sodium hydroxide, potassium hydroxide, ammonia, and so forth.

The biodegradable implant 1 fabricated in the oxide-layer forming step SA2 is satisfactorily washed, subjected to sterilization treatment, and is then used for implanting.

With the biodegradable implant 1 fabricated in this way, it is possible to suppress the rapid generation of hydrogen gas by preventing the corrosion of the implant substrate 2 by means of the oxide layer 4 that coats the outermost side in a living organism. Furthermore, even after the oxide layer 4 is lost, the corrosion of the implant substrate 2 is continued to be prevented by the intermediate layer 3 existing beneath the oxide layer 4, and thus, it is possible to continue to suppress the rapid generation of hydrogen gas.

Note that, although the anodic oxide layer has mainly been described in this embodiment as a method of forming the oxide layer 4, other film forming methods, such as vapor deposition, a high-temperature reaction, and so forth, may be employed so long as a sufficiently dense oxide layer 4 can be formed. In addition, the oxide layer 4 may be formed of any material so long as it has satisfactory biocompatibility and the corrosion thereof in a living organism is sufficiently slower than that of the magnesium alloy. Therefore, when forming the oxide layer 4 by a method other than the anodic oxidation treatment, an oxide other than the magnesium oxide, for example, an oxide layer 4 whose main component is calcium phosphate, may be employed.

In addition, in this embodiment, a case in which the implant substrate 2 contains the non-magnesium metals that dissolve in the acidic solution and the intermediate layer 3 is formed by subjecting the implant substrate 2 to the acid treatment has been described; however, in the case in which the implant substrate contains non-magnesium metals that dissolve in a basic solution, the acid treatment may be replaced with base treatment.

Example of Second Embodiment

Next, an Example of the above-described second embodiment will be described with reference to FIGS. 13 to 18.

A magnesium alloy used as the material for an implant substrate in this Example is a WE43 alloy that contains yttrium, neodymium, and rare earth elements as additives.

First, by immersing the implant substrate in 2.2 wt % aqueous phosphoric acid solution for one minute, the surface of the implant substrate was subjected to acid treatment (acid treating step or SB1). Next, the implant substrate is washed with ion-exchanged water (SB2), and the implant substrate was subjected to neutralization by washing it with 18 wt % aqueous sodium hydroxide solution (SB3).

Figure 14:
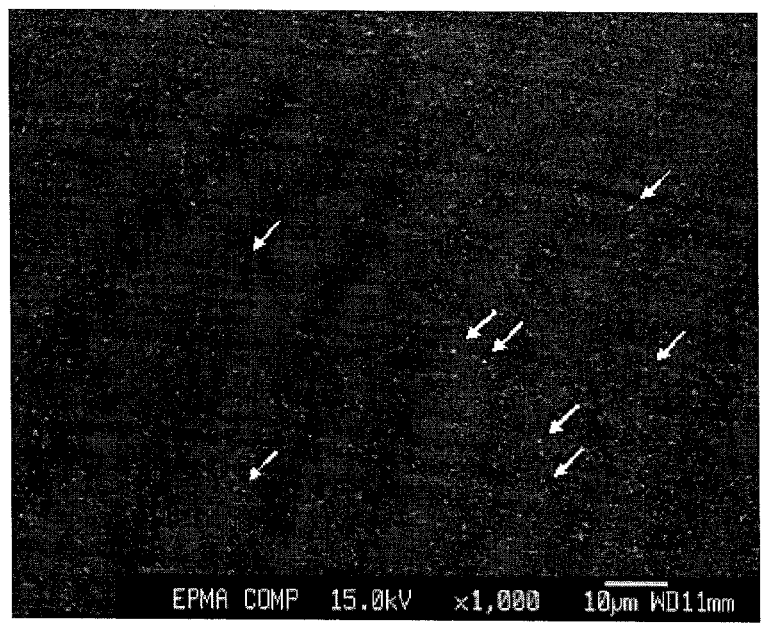
FIG. 14 is a scanning electron micrograph of an implant substrate before treatment with an aqueous phosphoric acid solution.
Figure 15:
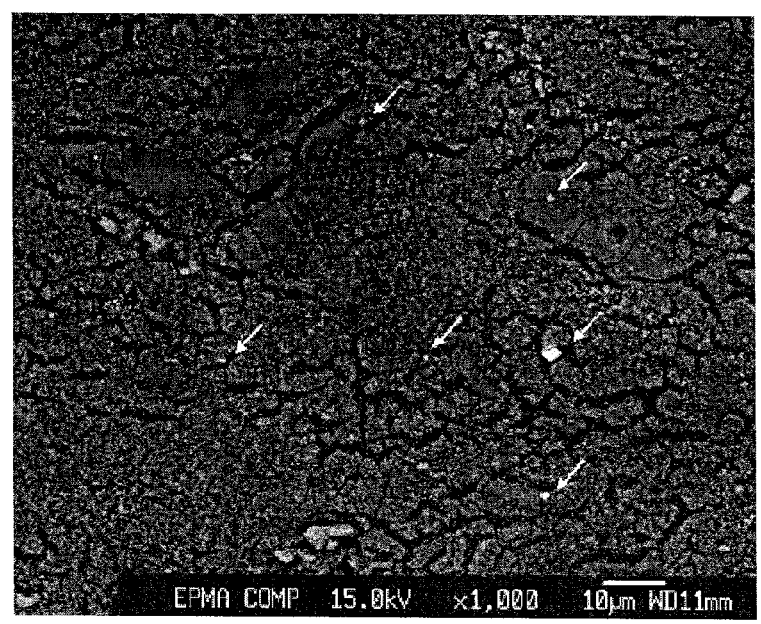
FIG. 15 is a scanning electron micrograph of the implant substrate after treatment with the aqueous phosphoric acid solution.

Here, the results of observing the surface of the implant substrate by using a scanning electron microscope before treatment with the aqueous phosphoric acid solution and after the treatment are shown in FIG. 14 and FIG. 15, respectively. In the figures, white dots indicated by arrows are yttrium particles. In FIG. 14, it is found that the yttrium particles are evenly dispersed over the entire surface. On the other hand, in FIG. 15, it is found that the number of the yttrium particles is reduced as compared with FIG. 14.

Figure 16:
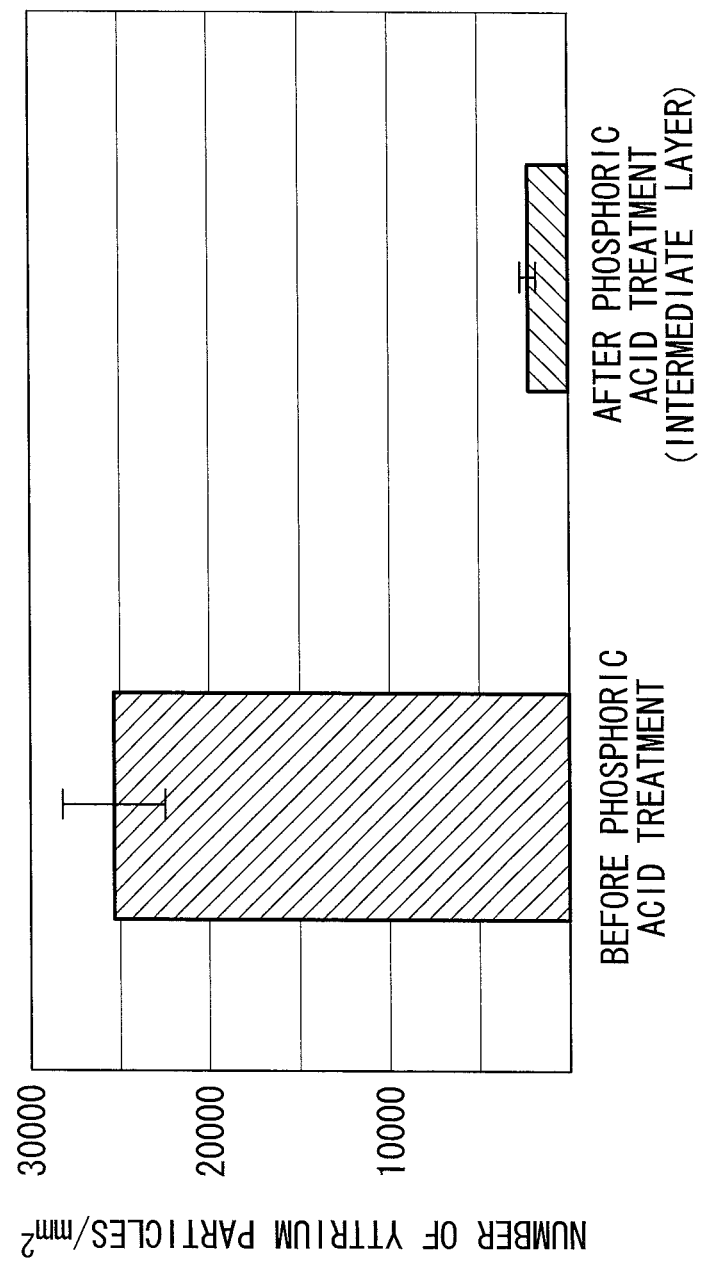
FIG. 16 is a graph showing the number of yttrium particles at a surface layer of the implant substrate before and after treatment with the aqueous phosphoric acid solution.

FIG. 16 is a graph showing measurement results of the number of the yttrium particles per unit area ($1\ mm^2$) of the surface of the implant substrate before and after treating it with the aqueous phosphoric acid solution. It was confirmed that, by treating the implant substrate with phosphoric acid, the yttrium particles at the surface layer of the implant were removed, reaching 1/10 or less of the amount before the phosphoric acid treatment.

Next, the anodic oxidation treatment was applied to the implant substrate (oxide-layer forming step or SB4). The composition of the electrolyte solution was 0.25 mol/L phosphoric acid and 1.5 mol/L ammonia, and the pH of the electrolyte solution was set to be 11. By applying a 200 V DC voltage between the electrodes for five minutes, an anodic oxide layer was formed on the surface of the implant substrate.

Next, the implant substrate was washed with ion-exchanged water (SB5); the residual electrolyte solution on the surface of the implant substrate was neutralized by washing with an aqueous nitric acid solution (SB6); and the implant substrate was washed again with ion-exchanged water (SB7).

The biodegradable implant according to this Example was fabricated by the method described above.

Next, a salt spray test was performed in order to assess the corrosion characteristics of the fabricated biodegradable implant according to this Example. Specifically, after exposing the intermediate layer by physically peeling off the anodic oxide layer of the biodegradable implant, the salt spray test was performed for ten days. For the salt spray test, 5 wt % aqueous sodium chloride solution adjusted to pH=7.0 was used. As a Comparative Example for comparison with the biodegradable implant according to this Example, the salt spray test was also performed under the same conditions on a biodegradable implant formed of the WE43 alloy in which no treatment has been applied to the surface thereof.

Figure 17:
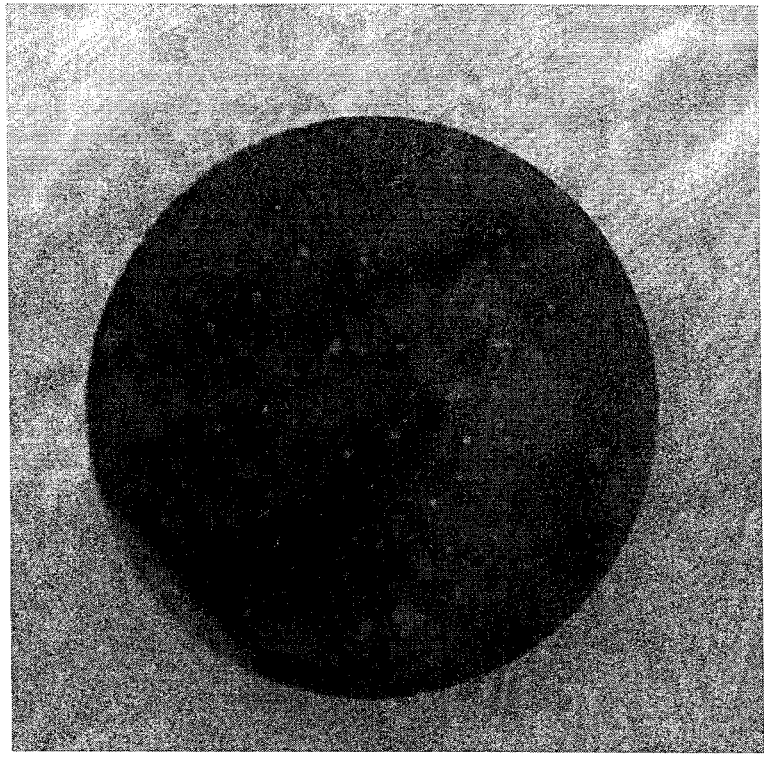
FIG. 17 is a photomicrograph showing the result of subjecting the biodegradable implant fabricated by the fabrication method shown in FIG. 13 to a salt spray test for ten days after physically removing an oxide layer thereof.
Figure 18:
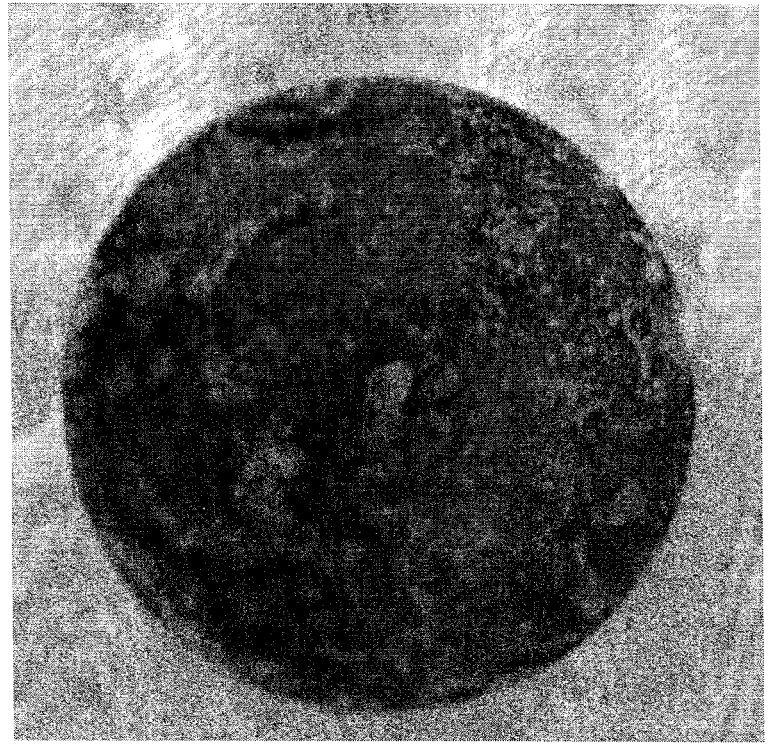
FIG. 18 is a photomicrograph showing the result of subjecting a biodegradable implant formed of a magnesium alloy and whose surface is untreated to a salt spray test for ten days.

FIG. 17 shows the test result for the biodegradable implant according to this Example, and FIG. 18 shows the test result for the biodegradable implant according to the Comparative Example. After the salt spray test, dot-like corroded portions were found on the biodegradable implant according to this Example. The area of these corroded portions, in total, accounted for about 10% of the total surface area of the biodegradable implant. On the other hand, corroded portions were found over the entire surface of the biodegradable implant according to the Comparative Example after the salt spray test. The area of these corroded portions, in total, accounted for about 90% of the total surface area of the biodegradable implant. In other words, the corrosion rate of the intermediate layer provided in the biodegradable implant according to this Example was about 1/9 of the corrosion rate of the implant substrate.

Based on these results, it was confirmed that the intermediate layer provided in the biodegradable implant according to the present invention possesses sufficient corrosion resistance, and thus, even if the oxide layer is not present, the implant substrate, that is, the base material, can be protected from corrosion over a sufficiently long period of time, making it possible to effectively suppress the rapid generation of hydrogen.

As has been described above, the first and second embodiments of the present invention have been described in detail with reference to the drawings; however, specific configurations are not limited to these embodiments, and design alterations or the like within a range that does not depart from the scope of the present invention are also encompassed.

For example, in the first and second embodiments, the high-purity magnesium layer and the anodic oxide layer are employed as coating layers to be formed on the surfaces of the implant substrates 2, 10, and 11; however, the coating layers may be of other types so long as the degradation rates of the implant substrates [2?] 10 and 11 in a living organism can be reduced.

In addition, the conditions for the anodic oxidation treatment are not limited to the conditions described above, and any conditions may be used so long as anodic oxide layers can be formed on the surfaces of the implant substrates 2, 10, and 11.

The following inventions are derived from the first and second embodiments described above.

A first aspect of the present invention is a biodegradable implant including a biodegradable magnesium member formed of a magnesium alloy; and a coating layer that coats the biodegradable magnesium member, thereby reducing a degradation rate thereof in a living organism, wherein a depression to be infiltrated by an osteoblast is formed in a surface of the biodegradable magnesium member.

With the first aspect of the present invention, the degradation rate of the biodegradable magnesium member in a living organism is kept lower than that of the coating layer formed on the surface of the biodegradable magnesium member. Accordingly, the concentration of hydrogen gas generated when the biodegradable magnesium member degrades in the living organism is kept low, and thus, the present invention can suitably be used even in a site where hydrogen gas is metabolized slowly, such as the osseous tissue.

With the above-described first aspect, the configuration thereof may be such that the coating layer includes a high-purity magnesium layer that is formed mainly of magnesium and whose content rate of a metal other than magnesium is lower than that in the biodegradable magnesium member.

The oxidation-reduction reaction between different types of metals is one of the corrosion reactions of a magnesium alloy. Specifically, in a magnesium alloy, a secondary battery is formed due to a contact between magnesium and the metal other than magnesium (electrically more noble metal than magnesium), thus advancing ionization of magnesium. With this configuration, the surface of the biodegradable magnesium member, which is a base material, is provided with the high-purity magnesium layer in which the number of sites that induce the above-described oxidation-reduction reaction is decreased by decreasing the content rate (number of metal particles) of the metal other than magnesium. In other words, the above-described oxidation-reduction reaction in the base material is suppressed by the high-purity magnesium layer. By doing so, a rapid corrosion of the base material formed of the magnesium alloy can be prevented, and the biodegradation thereof can occur while suppressing a rapid generation of hydrogen.

In the above-described configuration, the biodegradable magnesium member may be formed of a magnesium alloy containing an electrically more noble metal than magnesium, and the high-purity magnesium layer may be formed by removing particles of the electrically noble metal contained in the magnesium alloy from a surface layer of the biodegradable magnesium member. The biodegradable magnesium member may be formed of a magnesium alloy containing a rare earth, and the high-purity magnesium layer may be formed by removing particles of the rare earth contained in the magnesium alloy from a surface layer of the biodegradable magnesium member.

By coating the surface layer which is part of the biodegradable magnesium member in this way, it is possible to maintain a stable presence of the coating layer on the surface of the biodegradable magnesium member.

Here, it is preferable that a contained amount of particles of the electrically noble metal or particles of the rare earth contained in the magnesium alloy after removal thereof be 1/10 or less of a contained amount before the removal. By doing so, the corrosion rate of the coating layer can sufficiently be retarded.

In the above-described configuration provided with the high-purity magnesium layer, the biodegradable magnesium member may be formed of a magnesium alloy containing yttrium, and the high-purity magnesium layer may be formed by removing the yttrium contained in the magnesium alloy from a surface layer of the biodegradable magnesium member.

In the above-described first aspect, the coating layer may be provided with an oxide layer formed of an oxide at the outermost side.

By placing the highly corrosion resistant oxide layer, at the outermost side among the coating layers that coat the biodegradable magnesium member in this way, the generation of hydrogen can be suppressed even more effectively.

In the above-described configuration in which the oxide layer is provided, the oxide layer may be an anodic oxide layer that is formed by subjecting the biodegradable magnesium member to anodic oxidation.

By doing so, the anodic oxide layer, which is the oxide layer formed mainly of magnesium oxide, can be formed in a simple manner.

In the configuration in which an anodic oxide layer is provided as the oxide layer, it is preferable that the anodic oxide layer contain phosphorus.

By forming the oxide layer in the form of an anodic oxide layer containing phosphorus, it is possible to enhance the corrosion resistance of the biodegradable magnesium member, and thus, the degradation rate in a living organism can be kept low. Accordingly, the concentration of hydrogen gas generated in a living organism when the biodegradable magnesium member degrades can be kept low, and thus, it is possible to suppress the influence of hydrogen gas on treatment effects. Note that because phosphorus is a biological substance, it possesses biocompatibility.

In the above-described first aspect, it is preferable that the depression be formed so that a width or diameter thereof is 30 μm or greater and 300 μm or less, and it is preferable that a depth thereof be 30 μm or greater and 300 μm or less.

By doing so, cells such as osteoblasts or the like can infiltrate the depression, and thus, bone formation can be promoted. In particular, by designing the dimension of the depression as described above, it is possible to make osteoblasts effectively infiltrate the depression, and, in addition, it is possible to ensure a sufficient strength of the biodegradable implant.

In the above-described configuration provided with the depression, the depression may be a groove formed in a surface of the biodegradable magnesium member.

By doing so, it is possible to easily form the depression in the surface of the biodegradable magnesium member by means of machining or the like.

Here, a plurality of the grooves are formed in the surface of the biodegradable magnesium member in a lattice-like manner.

By doing so, it is possible to easily form the depression in the surface of the biodegradable magnesium member by means of machining or the like, and it is also possible to promote bone formation by making osteoblasts effectively infiltrate the depression.

In the above-described configuration provided with the depression, the depression may be a hole formed in a surface of the biodegradable magnesium member.

By employing such a depression, it is possible to easily form the depression in the surface of the biodegradable magnesium member by means of machining or the like.

Here, a communicating hole that joins a plurality of the holes may be provided.

By providing such a communicating hole, it is possible to promote bone formation by making osteoblasts effectively infiltrate the depression.

The configuration of the above-described first aspect may be such that a screw-thread-like protrusion is formed at a surface of the biodegradable magnesium member.

By doing so, it is possible to secure the biodegradable implant to a bone by engaging the screw-thread-like protrusion with the bone.

Here, the protrusion may be formed in an axial direction of the biodegradable magnesium member at a pitch of 1 mm or less.

By doing so, it is possible to ensure a desired securing force when the biodegradable implant is secured to a bone.

In the above-described first aspect, the coating layer may be formed of an element having a high biocompatibility.

A second aspect of the present invention is a biodegradable implant fabrication method including a coating step of coating a surface of a biodegradable magnesium member formed of a magnesium alloy with a coating layer that reduces a degradation rate in a living organism, and a depression forming step of forming a depression to be infiltrated by an osteoblast in a surface of the biodegradable magnesium member before the coating step.

With the second aspect of the present invention, the above-described biodegradable implant can be fabricated. With the biodegradable implant fabricated in this way, the degradation rate of the biodegradable magnesium member in a living organism is kept lower than that of the coating layer that coats the surface of the biodegradable magnesium member. Accordingly, the concentration of hydrogen gas generated when the biodegradable magnesium member degrades in the living organism is kept low, and thus, the present invention can suitably be used even in a site where hydrogen gas is metabolized slowly, such as the osseous tissue.

The configuration of the above-described second aspect may be such that the coating step includes a high-purity magnesium layer forming step of forming a high-purity magnesium layer that is formed mainly of magnesium and whose content rate of a metal other than magnesium is lower than that in the biodegradable magnesium member.

In this configuration, the high-purity magnesium layer forming step may include an acid treating step of treating a surface of the biodegradable magnesium member with an acidic solution.

By doing so, in the acid treating step, the high-purity magnesium layer can be formed in a simple manner by removing the metal other than magnesium (non-magnesium metal) contained in the magnesium alloy at the surface layer of the biodegradable magnesium member. In order to enhance the biocompatibility of the biodegradable implant, it is preferable that the acidic solution be an acid possessing biocompatibility, and it is more preferable that the acidic solution be an aqueous solution of hydrochloric acid, acetic acid, formic acid, nitric acid, or phosphoric acid.

The configuration of the above-described second aspect may be such that the coating step includes an oxide-layer forming step of coating the biodegradable magnesium member with an oxide layer formed of an oxide.

In this configuration, in the oxide-layer forming step, the biodegradable magnesium member may be subjected to an anodic oxidation treatment in an electrolyte solution.

Here, the electrolyte solution may contain phosphate ions.

By doing so, an anodic oxide layer containing phosphorus is formed, and thus, it is possible to enhance the corrosion resistance of the anodic oxide layer.

Furthermore, the electrolyte solution may be such that it contains 0.2 mol/L or greater and 1 mol/L or less phosphoric acid and 0.2 mol/L or greater and 5 mol/L or less ammonia or ammonium ion, does not contain elemental fluorine, and has a pH of 9 or greater and 13 or less.

By doing so, it is possible to form an anodic oxide layer having sufficient corrosion resistance.

In the above-described configuration including the oxide-layer forming step, the oxide layer may contain 35 wt % or greater and 65 wt % or less elemental magnesium, 25 wt % or greater and 45 wt % or less elemental oxygen, and 4 wt % or greater and 15 wt % or less elemental phosphorus.

By doing so, it is possible to further enhance the corrosion resistance of the anodic oxide layer.

In the above-described second aspect, in the depression forming step, the depression may be formed in the surface of the biodegradable magnesium member by means of hot working.

By doing so, it is possible to easily form the depression in the surface of the biodegradable magnesium member.

The above-described second aspect may include a heat treating step of subjecting the biodegradable magnesium member to a heat treatment.

By subjecting the biodegradable magnesium member to the heat treatment, components of the biodegradable magnesium member are made uniform, and thus, it is possible to reduce the variability in the degradation rate of the biodegradable magnesium member in a living organism. In addition, it is possible to enhance the strength of the biodegradable magnesium member.

REFERENCE SIGNS LIST 1 biodegradable implant
2, 10, 11 implant substrate (biodegradable magnesium member)
3 intermediate layer (coating layer, high-purity magnesium layer)
4 oxide layer, anodic oxide layer (coating layer)
12 protrusion
13 depression
14 hole
SA1, SB1 acid treating step (high-purity magnesium layer forming step)
SA2, SB4, SC3 anodic oxide-layer forming step
SC1 depression forming step
SC2 heat treating step

The invention claimed is:

1. A biodegradable implant comprising:
a biodegradable magnesium member formed of a magnesium alloy; and
a coating layer that coats the biodegradable magnesium member, thereby reducing a degradation rate thereof in a living organism, wherein
a depression to be infiltrated by an osteoblast is formed in a surface of the biodegradable magnesium member, wherein
the coating layer includes:
a high-purity magnesium layer that is formed of magnesium and a metal other than magnesium, a content rate of the metal other than magnesium is lower than a content rate of the metal in the biodegradable magnesium member, and
an oxide layer provided at an outermost side and formed of an oxide,
wherein the content rate of the metal other than magnesium in the coating layer is equal to or less than $1/10$ of the content rate of the metal other than magnesium in the biodegradable magnesium member.

2. The biodegradable implant according to claim 1, wherein the biodegradable magnesium member is formed of a magnesium alloy containing an electrically more noble metal than magnesium, and
the high-purity magnesium layer is formed by removing particles of the electrically noble metal contained in the magnesium alloy from a surface layer of the biodegradable magnesium member.

3. The biodegradable implant according to claim 1, wherein the biodegradable magnesium member is formed of a magnesium alloy containing a rare earth element, and
the high-purity magnesium layer is formed by removing particles of the rare earth element contained in the magnesium alloy from a surface layer of the biodegradable magnesium member.

4. The biodegradable implant according to claim 2, wherein the biodegradable magnesium member is formed of a magnesium alloy containing yttrium, and
the high-purity magnesium layer is formed by removing the yttrium contained in the magnesium alloy from a surface layer of the biodegradable magnesium member.

5. The biodegradable implant according to claim 3, wherein the biodegradable magnesium member is formed of a magnesium alloy containing yttrium, and
the high-purity magnesium layer is formed by removing the yttrium contained in the magnesium alloy from a surface layer of the biodegradable magnesium member.

6. The biodegradable implant according to claim 2, wherein a contained amount of the particles in the high-purity magnesium layer after the particles have been removed from the high-purity magnesium layer is $1/10$ or less of a contained amount thereof before the removal.

7. The biodegradable implant according to claim 3, wherein a contained amount of the particles in the high-purity magnesium layer after the particles have been removed from the high-purity magnesium layer is $1/10$ or less of a contained amount thereof before the removal.

8. The biodegradable implant according to claim 1, wherein the oxide layer is an anodic oxide layer that is formed by subjecting the biodegradable magnesium member to anodic oxidation.

9. The biodegradable implant according to claim 8, wherein the anodic oxide layer contains phosphorus.

10. The biodegradable implant according to claim 1, wherein the depression is formed so that a width or diameter thereof is 30 µm or greater and 300 µm or less.

11. The biodegradable implant according to claim 1, wherein the depression is formed so that a depth thereof is 30 µm or greater and 300 µm or less.

12. The biodegradable implant according to claim 1, wherein the depression is a groove formed in a surface of the biodegradable magnesium member.

13. The biodegradable implant according to claim 12, wherein a plurality of the grooves are formed in the surface of the biodegradable magnesium member in a lattice-like manner.

14. The biodegradable implant according to claim 1, wherein the depression is a hole formed in a surface of the biodegradable magnesium member.

15. The biodegradable implant according to claim 14, wherein a communicating hole that joins a plurality of the holes is provided.

16. The biodegradable implant according to claim 1, wherein a screw-thread-like protrusion is formed at a surface of the biodegradable magnesium member.

17. The biodegradable implant according to claim 16, wherein the protrusion is formed in an axial direction of the biodegradable magnesium member at a pitch of 1 mm or less.

18. The biodegradable implant according to claim 1, wherein the coating layer is formed of a biocompatible element.

* * * * *